United States Patent
Garcia Garcia et al.

(10) Patent No.: US 12,109,060 B2
(45) Date of Patent: Oct. 8, 2024

(54) NONINVASIVE ASSESSMENT OF MICROVASCULAR DYSFUNCTION

(71) Applicants: MEDSTAR HEALTH, INC., Columbia, MD (US); OXFORD UNIVERSITY HOSPITALS NHS FOUNDATION TRUST, Oxford (GB)

(72) Inventors: Hector Manuel Garcia Garcia, Columbia, DC (US); Giovanni Luigi De Maria, Oxford (GB); Adrian P. Banning, Oxford (GB)

(73) Assignees: MEDSTAR HEALTH, INC., Columbia, MD (US); OXFORD UNIVERSITY HOSPITALS NHS FOUNDATION TRUST, Headington (GB)

( * ) Notice: Subject to any disclaimer, the term of this patent is extended or adjusted under 35 U.S.C. 154(b) by 0 days.

(21) Appl. No.: 17/068,368

(22) Filed: Oct. 12, 2020

(65) Prior Publication Data
US 2021/0106239 A1  Apr. 15, 2021

Related U.S. Application Data

(60) Provisional application No. 62/913,431, filed on Oct. 10, 2019.

(51) Int. Cl.
*A61B 6/00* (2024.01)
*A61B 5/00* (2006.01)
(Continued)

(52) U.S. Cl.
CPC ........ *A61B 6/5217* (2013.01); *A61B 5/02007* (2013.01); *A61B 5/02028* (2013.01);
(Continued)

(58) Field of Classification Search
None
See application file for complete search history.

(56) References Cited

U.S. PATENT DOCUMENTS 9,538,925 B2  1/2017 Sharma et al.
9,700,219 B2  7/2017 Sharma et al.
(Continued)

OTHER PUBLICATIONS

Koltowski et al., "Quantitative flow ratio derived from diagnostic coronary angiography in assessment of patients with intermediate coronary stenosis: a wirefree fractional flow reserve study," (Aug. 20, 2018), Clin Res Cardiol 107, 858-867. (Year: 2018).*

Zhang, Zhang, Shigeho Takarada, and Sabee Molloi. "Quantification of coronary microvascular resistance using angiographic images for volumetric blood flow measurement: in vivo validation." American Journal of Physiology—Heart and Circulatory Physiology 300.6 (2011): H2096-H2104.

(Continued)

*Primary Examiner* — Joel Lamprecht
*Assistant Examiner* — Ashish S Jasani
(74) *Attorney, Agent, or Firm* — Tarolli, Sundheim, Covell & Tummino LLP (57) ABSTRACT

Systems and methods are provided for assessing microvascular dysfunction of a patient. A series of images is acquired of a region of interest within the body of the patient. An imaging-derived index of microcirculatory resistance is determined from the series of images. A clinical parameter representing microvascular dysfunction is assigned to the patient via a predictive model according to at least the imaging-derived index of microcirculatory resistance.

1 Claim, 4 Drawing Sheets

(51) Int. Cl.
 *A61B 5/02* (2006.01)
 *A61B 6/50* (2024.01)
(52) U.S. Cl.
 CPC .......... *A61B 5/4839* (2013.01); *A61B 5/7275* (2013.01); *A61B 6/481* (2013.01); *A61B 6/504* (2013.01)

(56) References Cited

U.S. PATENT DOCUMENTS

| | | |
|---|---|---|
| 2008/0292049 A1 | 11/2008 | Camus et al. |
| 2010/0241404 A1 | 9/2010 | Taylor et al. |
| 2014/0314676 A1 | 10/2014 | Spino et al. |
| 2015/0245775 A1 | 9/2015 | Fonte et al. |
| 2017/0032097 A1* | 2/2017 | Itu .......................... G16H 50/50 |
| 2018/0253531 A1* | 9/2018 | Sharma .................. G16H 30/40 |
| 2018/0276817 A1 | 9/2018 | Isgum et al. |
| 2019/0000554 A1* | 1/2019 | Taylor ..................... G06T 11/00 |
| 2019/0110776 A1* | 4/2019 | Yu ......................... A61B 5/0035 |

OTHER PUBLICATIONS

Yong, Andy S., et al. "Calculation of the index of microcirculatory resistance without coronary wedge pressure measurement in the presence of epicardial stenosis." JACC: Cardiovascular Interventions 6.1 (2013): 53-58.

King, Zhenhua, et al. "Diagnostic performance of qfr for the evaluation of intermediate coronary artery stenosis confirmed by fractional flow reserve." Brazilian journal of cardiovascular surgery 34.2 (2019): 165-172.

Mejia-Renteria, Hernan, et al. "Influence of microcirculatory dysfunction on angiography-based functional assessment of coronary stenoses." JACC: Cardiovascular Interventions 11.8 (2018): 741-753.

PCT International Search Report and Written Opinion for corresponding International Application Serial No. PCT/US2020/055240, mailed Jan. 29, 2021, pp. 1-10.

European Search Report for Corresponding Application Serial No. 20875626.2, Dated Aug. 11, 2022, pp. 1-10.

* cited by examiner

NONINVASIVE ASSESSMENT OF MICROVASCULAR DYSFUNCTION

RELATED APPLICATIONS

This application claims priority from U.S. Provisional Application No. 62/913,431, filed 10 Oct. 2019, the subject matter of which is incorporated herein by reference in its entirety.

TECHNICAL FIELD

This invention relates to diagnostic systems, and more particularly, to noninvasive assessment of microvascular dysfunction.

BACKGROUND

Coronary microvascular dysfunction (CMD) often remains under-diagnosed in patients with coronary artery disease, despite its well reported clinical and prognostic implications. Various methods have been proposed to aid the diagnosis of CMD in the catheterization laboratory. Among them, the index of microcirculatory resistance (IMR) has gained particular attention. However, the application of invasive coronary physiology to assess the extent of CMD remains very limited in routine clinical practice. This is partly due to the required additional procedural time, costs and technical complexity mainly related with pressure-wire manipulation and need of adenosine infusion to achieve maximal hyperaemia.

SUMMARY OF THE INVENTION

In one example, a method is provided for assessing microvascular dysfunction of a patient. A series of images is acquired of a region of interest within the body of the patient. An imaging-derived index of microcirculatory resistance is determined from the series of images. A clinical parameter representing microvascular dysfunction is assigned to the patient via a predictive model according to at least the imaging-derived index of microcirculatory resistance.

In another example, a system is provided. The system includes a processor and a non-transitory memory storing computer executable instructions for assessing coronary microvascular dysfunction of a patient. The executable instructions are executable by the processor to provide a device interface that receives a series of images of at least a portion of a chest of the patient and a feature extractor that determines a set of features associated with the patient. The set of features includes at least an angiography-derived index of microcirculatory resistance from the series of images. A predictive model assigns a clinical parameter to the patient according to the set of features.

In yet another example, a method is provided for assessing coronary microvascular dysfunction of a patient. A first series of images is acquired of a region of interest within the patient, and a first angiography-derived index of microcirculatory resistance is determined from the series of images. A first clinical parameter is assigned to the patient via a first predictive model according to at least the first angiography-derived index of microcirculatory resistance. The first clinical parameter is a categorical parameter that can assume a first value representing a presence of microvascular dysfunction, a second value representing an absence of microvascular dysfunction, and a third value representing an indeterminate result.

If the first clinical parameter assumes the third value, a vasodilator is provided to the patient and a second series of images of the region of interest is acquired. A second angiography-derived index of microcirculatory resistance is determined from the second series of images, and a second clinical parameter is assigned to the patient via a second predictive model according to at least the second angiography-derived index of microcirculatory resistance. The second clinical parameter is a categorical parameter that can assume a first value representing the presence of microvascular dysfunction and a second value representing the absence of microvascular dysfunction.

DETAILED DESCRIPTION

The phrase "patient data," as used herein, is intended to encompass categorical and continuous values describing the current physical or mental state of a patient.

The phrase "microvascular dysfunction" refers to any pathology that may disrupt the microvasculature within the body, including endothelial dysfunction, coronary spasm, inflammation, and atherosclerosis.

The phrase "therapeutic intervention" refers to any medical treatment applied to treat or mitigate the effects of microvascular dysfunction. Therapeutic interventions can include, for example, administration of medications and implantations of medical devices.

As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

Figure 1:
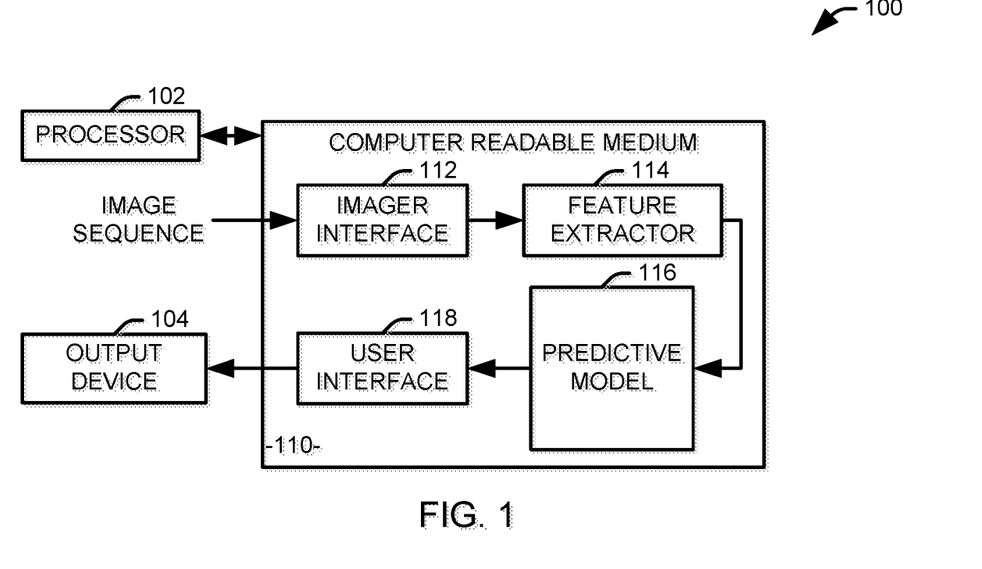
FIG. 1 illustrates a diagnostic system for evaluating a patient for microvascular dysfunction.

FIG. 1 illustrates a diagnostic system 100 for evaluating a patient for microvascular dysfunction. The system 100 includes a processor 102, an output device 104, and a non-transitory memory 110 storing computer executable instructions for assessing microvascular dysfunction for a patient. The machine executable instructions include, for example, an image interface 112 that is configured to receive a sequence of medical images of a region of interest within the patient from a medical scanner (not shown), a remote system storing medical images, or a local storage medium.

Depending on the source of the images, the image interface 112 can include, for example, software for interacting with appropriate hardware for implementing a bus or network connection with the source of the sequence of images. Examples of medical scanners that could be used with the system include optical coherence tomography (OCT) images, intravascular ultrasound imagers, computed tomography (CT) imagers, and similar devices. In one implementation, the medical scanner can provide sequences of X-ray images to the imager interface.

A feature extractor 114 determines a set of features associated with the patient that are relevant to assessment of microvascular dysfunction. The set of features includes a non-invasive, imaging-derived index of microcirculatory resistance that is determined from the series of images of the region of interest. In one example, the feature extractor 114 can calculate the non-invasive, imaging derived index of microcirculatory resistance by determining, from the series of images, a distal pressure at a distal part of a target vessel, for example, beyond a vascular lesion, and a transit time of a marker to travel between first and second reference points, and then calculating a product of the transit time and the imaging derived distal pressure.

The feature extractor 114 can also extract patient data from an electronic health records database (not shown) or receive biometric parameters from associated sensors (not shown) that are useful for assessment of microvascular dysfunction. Examples of relevant patient data can include a categorical parameters representing the patient's status as a smoker or non-smoker, a diagnosis of diabetes, a diagnosis of hypertension, and a diagnosis of elevated cholesterol, as well as continuous parameters representing current and past values of blood pressure, pulse, blood glucose levels, and similar parameters.

A predictive model 116 that assigns a clinical parameter to the patient according to the set of features extracted at the feature extractor 114. The clinical parameter can be provided as any value representing the presence or absence of microvascular dysfunction, either generally or within a specific region of the body, a degree of microvascular dysfunction in the patient, a likelihood of microvascular dysfunction, either generally or within a specific region of the body, the expected or actual efficacy of a specific therapeutic intervention for microvascular dysfunction, or a suggested therapeutic intervention for the patient. In one example, the clinical parameter is a categorical parameter that can assume a first value representing a presence of microvascular dysfunction, a second value representing an absence of microvascular dysfunction, or a third value representing an indeterminate result. In another example, the clinical parameter is continuous parameter representing a likelihood of coronary microvascular dysfunction. In still another example, the clinical parameter represents a likelihood of an adverse reaction if a therapeutic intervention is provided to the patient.

The predictive model 116 can utilize one or more pattern recognition algorithms, implemented, for example, as classification and regression models, each of which analyze the extracted features to assign a clinical parameter to the user. Where multiple classification and regression models are used, the predictive model 116 can include an arbitration element can be utilized to provide a coherent result from the various algorithms. Depending on the outputs of the various models, the arbitration element can simply select a class from a model having a highest confidence, select a plurality of classes from all models meeting a threshold confidence, select a class via a voting process among the models, or assign a numerical parameter based on the outputs of the multiple models. Alternatively, the arbitration element can itself be implemented as a classification model that receives the outputs of the other models as features and generates one or more output classes for the patient.

The predictive model 116, as well as any constituent models, can be trained on training data representing the various classes of interest. The training process of the predictive model 116 will vary with its implementation, but training generally involves a statistical aggregation of training data into one or more parameters associated with the output classes. Any of a variety of techniques can be utilized for the models, including support vector machines (SVMs), regression models, self-organized maps, fuzzy logic systems, data fusion processes, boosting and bagging methods, rule-based systems, or artificial neural networks (ANNs).

For example, an SVM classifier can utilize a plurality of functions, referred to as hyperplanes, to conceptually divide boundaries in the N-dimensional feature space, where each of the N dimensions represents one associated feature of the feature vector. The boundaries define a range of feature values associated with each class. Accordingly, an output class and an associated confidence value can be determined for a given input feature vector according to its position in feature space relative to the boundaries. An SVM classifier utilizes a user-specified kernel function to organize training data within a defined feature space. In the most basic implementation, the kernel function can be a linear function, although the systems and methods described herein can utilize any of several linear or non-linear kernel functions.

An ANN classifier comprises a plurality of nodes having a plurality of interconnections. The values from the feature vector are provided to a plurality of input nodes. The input nodes each provide these input values to layers of one or more intermediate nodes. A given intermediate node receives one or more output values from previous nodes. The received values are weighted according to a series of weights established during the training of the classifier. An intermediate node translates its received values into a single output according to a transfer function at the node. For example, the intermediate node can sum the received values and subject the sum to a binary step function. A final layer of nodes provides the confidence values for the output classes of the ANN, with each node having an associated value representing a confidence for one of the associated output classes of the classifier.

A regression model applies a set of weights to various functions of the extracted features, most commonly linear functions, to provide a continuous result. In general, regression features can be categorical, represented, for example, as zero or one, or continuous. In a logistic regression, the output of the model represents the log odds that the source of the extracted features is a member of a given class. In a binary classification task, these log odds can be used directly as a confidence value for class membership or converted via the logistic function to a probability of class membership given the extracted features.

A rule-based classifier applies a set of logical rules to the extracted features to select an output class. Generally, the rules are applied in order, with the logical result at each step influencing the analysis at later steps. The specific rules and their sequence can be determined from any or all of training data, analogical reasoning from previous cases, or existing domain knowledge. One example of a rule-based classifier is a decision tree algorithm, in which the values of features in a feature set are compared to corresponding threshold in a hierarchical tree structure to select a class for the feature vector. A random forest classifier is a modification of the decision tree algorithm using a bootstrap aggregating, or "bagging" approach. In this approach, multiple decision trees are trained on random samples of the training set, and an average (e.g., mean, median, or mode) result across the plurality of decision trees is returned. For a classification task, the result from each tree would be categorical, and thus a modal outcome can be used, but a continuous parameter can be computed according to a number of decision trees that select a given task.

Regardless of the specific model employed, the clinical parameter generated at the predictive model 116 can be provided to a user at the output device 104 via a user interface 118 or stored on a non-transitory computer readable medium (e.g., 110), for example, in an electronic medical record associated with the patient.

Figure 2:
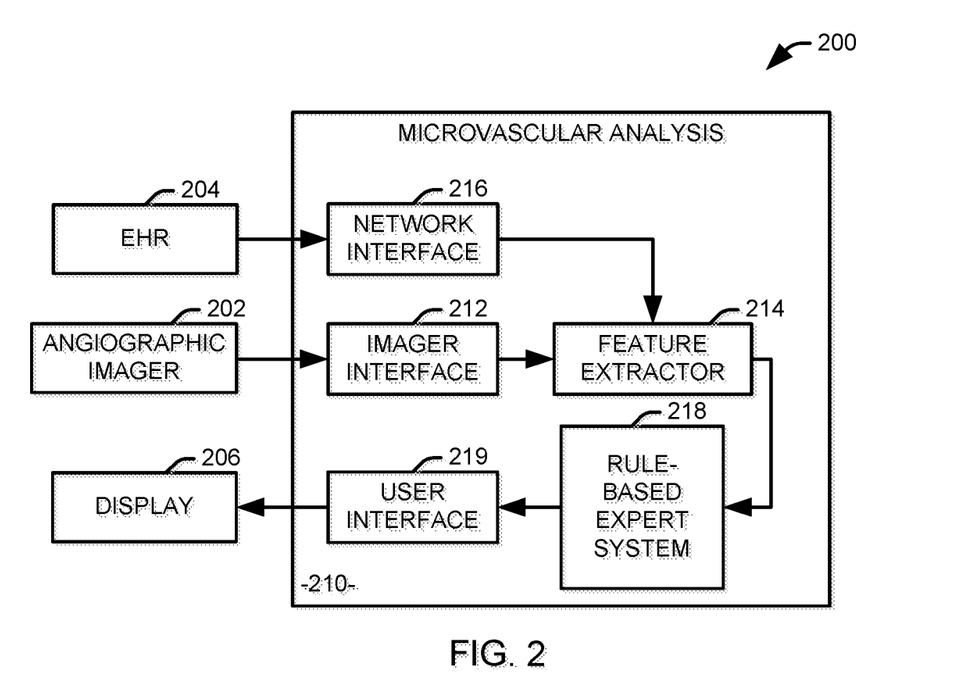
FIG. 2 illustrates one implementation of a diagnostic system for evaluating a patient for microvascular dysfunction.

FIG. 2 illustrates one implementation of a diagnostic system 200 for evaluating a patient for microvascular dysfunction. The system 200 includes an angiographic imaging system 202 configured to capture images of region of interest within the body. In one implementation, the angiographic imaging system 202 is implemented as a three-dimensional quantitative angiography system. Images from the angiographic imaging system 202 are then provided to a microvascular analysis system 210 at an imager interface 212. It will be appreciated that the microvascular analysis system 210 can either retrieve the images from a local or remote storage medium or receive the images directly from the angiographic imaging system 202, via a wired connection, a short range wireless connection (e.g., a Bluetooth connection), or over a local network. The analysis system 210 can be implemented as instructions stored on a machine-readable medium of a local, stand-alone computer system, as instructions stored on a server, with images provided via a network interface, or as software or firmware on the angiographic imaging system 202, such that the microanalysis system 210 and the angiographic imaging system 202 share hardware components.

In one example, the angiographic imaging system 202 acquires angiographic images at least twenty-five degrees apart were acquired at fifteen frames per second after a manual injection of a contrast dye or other marker visible to the angiographic imaging system 202. In one implementation, the images are captured at hyperaemia, for example, induced via achieved with intravenous infusion of adenosine or another vasodilatory agent. In another implementation, the images are captured at rest. It will be appreciated that a medical professional utilizing the system 200 can select between capturing images at hyperaemia or at rest based upon an evaluation of the patient and underlying conditions of the patient.

The images received at the imager interface 212 are provided to a feature extractor 214 that determines a non-invasive, imaging-derived index of microcirculatory resistance. In one example, the non-invasive, imaging-derived index of microcirculatory resistance is determined as a product of a pressure at a distal location, for example, a reference point within a distal vessel, and a transit time of the marker between two reference points, for example, an injection point and the distal location. In one implementation, the transit time is determined as a mean transit time across a plurality of injections of markers (e.g., contrast dye).

The pressure at the distal location can be difficult to measure directly, and in one implementation, an angiography-derived fractional flow reserve can be determined from the images and used as a proxy for the distal pressure. More specifically, the angiography-derived fractional flow reserve can serve as a proxy for the ratio of the distal pressure to the aortic pressure, which can be determined via direct measurement, for example, at the point at which the marker is injected into the bloodstream. The transit time can be determined from the number of frames necessary for the marker to travel between the reference points divided by the frame rate, for example, in frames per second, provided by the angiographic imaging system 202, in this example, fifteen. Accordingly, in one example, the non-invasive, imaging-derived index of microcirculatory resistance can be calculated as the product of the aortic pressure, the angiography-derived fractional flow reserve, and the ratio of the number of frames necessary for the marker to travel between the reference points to the frame rate of the imager.

One example of an angiography-derived fractional flow reserve is the quantitative flow ratio (QFR). Quantitative flow ratio is a novel angiography-based index derived from application of computational flow dynamics to three-dimensional modelling of the coronary artery. It has been shown to have a good correlation with invasive fractional flow reserve and it appears to be superior to angiography in assessing the ischemic potential of angiographically intermediate coronary stenosis. In one example, three-dimensional quantitative coronary angiography and QFR were measured offline using QAngio® XA 3D software by two independent operators blinded to clinical, IMR and cMRI data, with cases of disagreement resolved by consensus.

In the illustrated example, the feature extractor 214 can also retrieve patient data from one or more local or remote computer readable media associated with the system, including, for example, an electronic health records (EHR) database 204. To this end, in the illustrated implementation, the feature extractor 214 can communicate with remote systems via a network interface 216. The network interface 216 can include appropriate software and firmware for transmitting and receiving information via one or more hardware communications devices (not shown) associated with the system, such as a short-range transceiver (e.g., a Bluetooth transceiver), an Ethernet adapter, and a wireless (e.g., Wi-Fi) adapter. The feature extractor determining at least one feature of the set of features from the retrieved patient data, which can include, for example, categorical parameters representing the patient's status as a smoker, a diagnosis of diabetes, a diagnosis of hypertension, or a diagnosis of elevated cholesterol, as well as continuous parameters representing current and past values of blood pressure, pulse, blood glucose levels, and similar parameters.

A rule-based expert system 218 can determine a clinical parameter representing microvascular dysfunction within the patient from the extracted features. In the illustrated implementation, the clinical parameter is a categorical parameter that can assume any of a first value representing a presence of microvascular dysfunction, a second value representing an absence of microvascular dysfunction, and a third value representing an indeterminate result. The determined clinical parameter can then be displayed to a user via a user interface 219 at an associated display 206.

Figure 3:
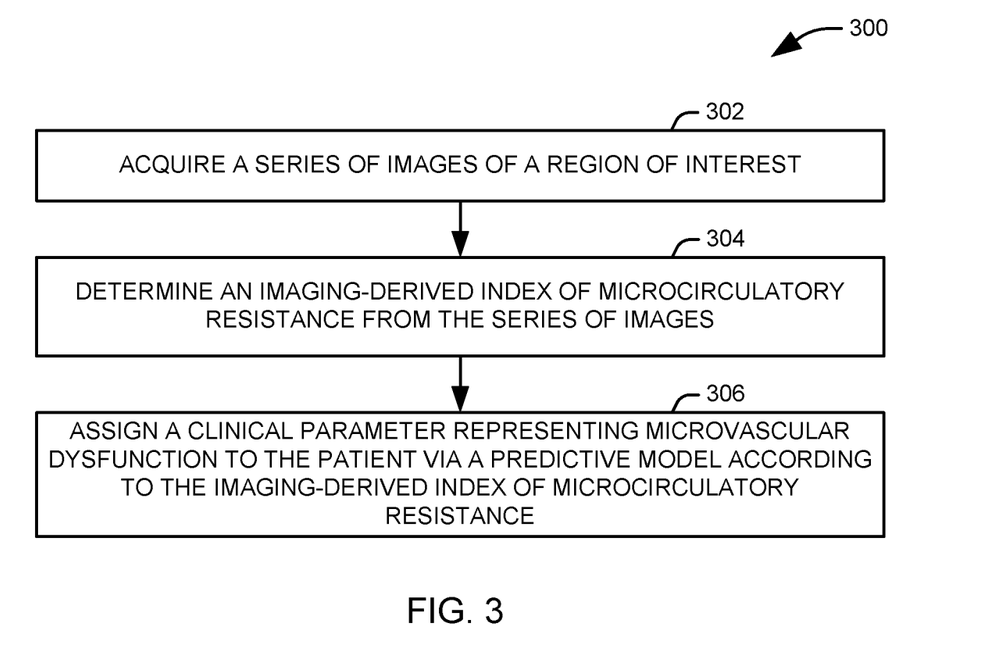
FIG. 3 illustrates a method for assessing microvascular dysfunction of a patient.
Figure 4:
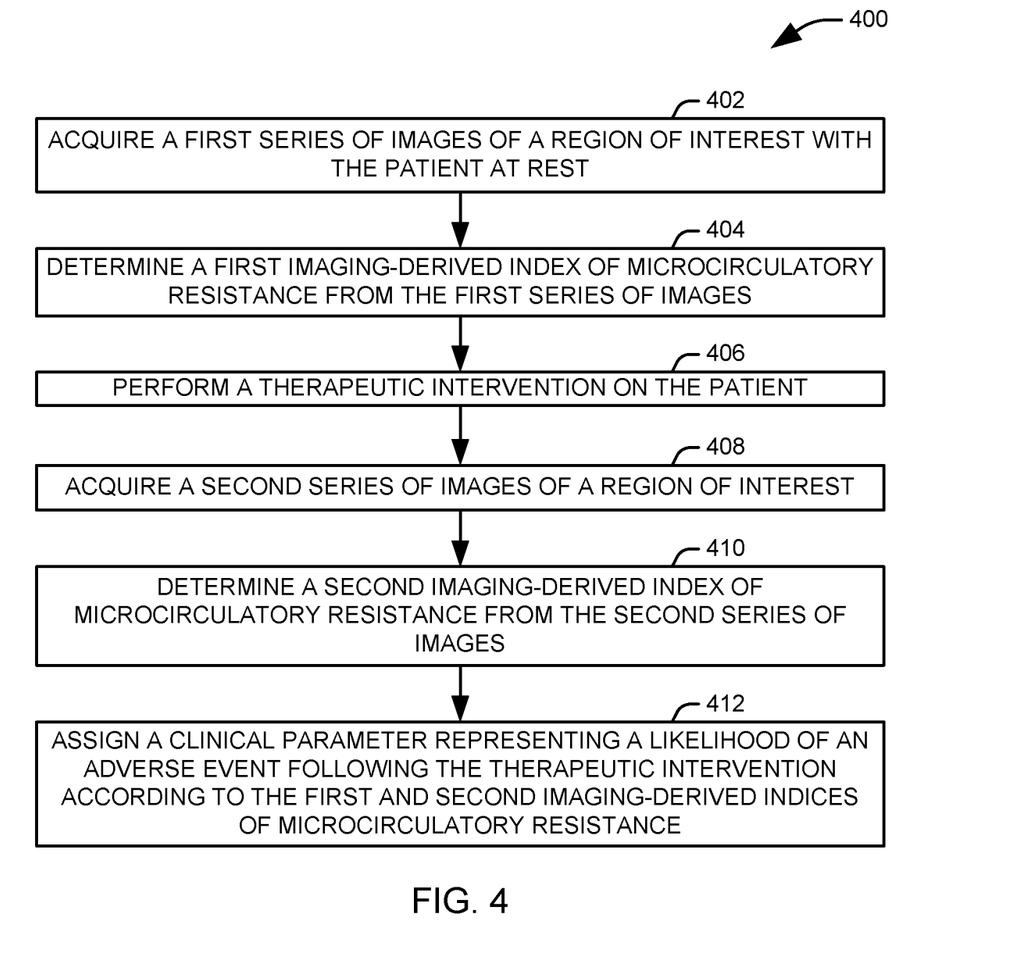
FIG. 4 illustrates one example of a method for assessing the results of a therapeutic intervention on the microvascular function of a patient.
Figure 5:
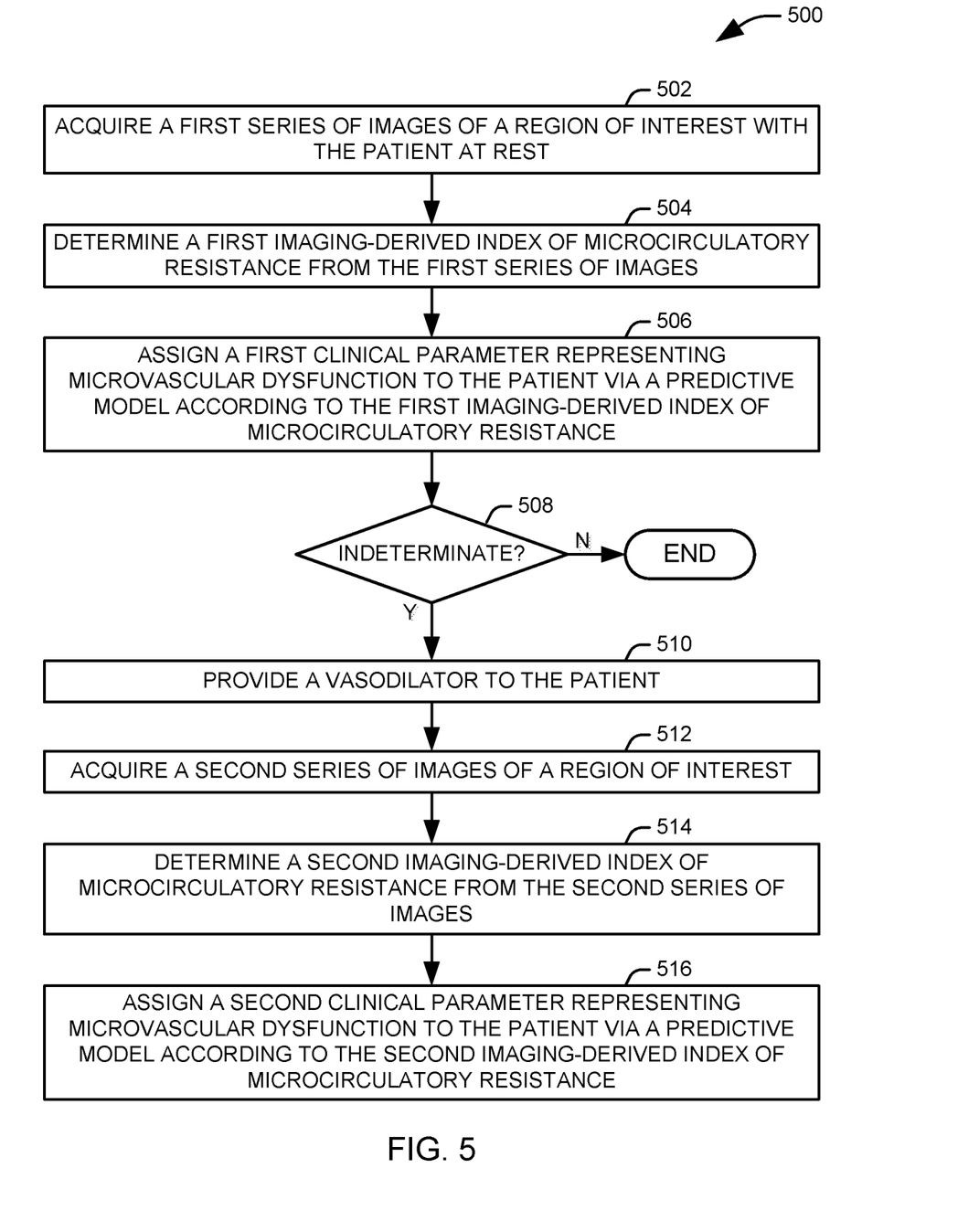
FIG. 5 illustrates an example of a method for assessing microvascular dysfunction of a patient.

In view of the foregoing structural and functional features described above, example methods will be better appreciated with reference to FIGS. 3-5. While, for purposes of simplicity of explanation, the example methods of FIGS. 3-5 are shown and described as executing serially, it is to be understood and appreciated that the present examples are not limited by the illustrated order, as some actions could in other examples occur in different orders, multiple times and/or concurrently from that shown and described herein.

Moreover, it is not necessary that all described actions be performed to implement a method.

FIG. 3 illustrates a method 300 for assessing microvascular dysfunction of a patient. At 302, a series of images of are acquired in a region of interest within the body of the patient. In one example, the region of interest is selected to include at least one vascular structure of interest. It will be appreciated that the series of images can be acquired with the patient at rest, that is, without providing a vasodilator to the patient, or after a vasodilator has been provided to the patient. Whether to provide the vasodilator to the patient can be determined according to a diagnosis of one or more underlying conditions of the patient. In one example, the region of interest is within a chest of the patient and the series of images is acquired when no vasodilator has been provided to the patient when the patient is diagnosed with ST segment elevation myocardial infarction, but a vasodilator is provided when the patient is diagnosed with non-ST-elevation acute coronary syndrome or chronic coronary syndrome. To assist in analysis of the images, an artificial marker, such as contrast dye, can be introduced to the patient prior to capturing the series of images.

At 304, an imaging-derived index of microcirculatory resistance is determined from the series of images. In one example, the imaging-derived index of microcirculatory resistance is calculated by determining a distal pressure at a distal location in a target vessel, for example, beyond a vascular lesion, from the series of images, determining a transit time of a natural or artificial marker to travel between first and second reference points, and calculating a product of the transit time and the imaging derived distal pressure. The transit time of the marker can be determined from the series of images as a ratio of a number of images in the series of images needed for the contrast dye to travel from the first reference point, for example, a guiding catheter, to the second reference point, for example, a distal reference associated with the distal vessel, to a frame rate associated with the series of images.

At 306, a clinical parameter representing microvascular dysfunction is assigned to the patient via a predictive model according to at least the imaging-derived index of microcirculatory resistance. The clinical parameter can be provided as any value representing the presence or absence of microvascular dysfunction, either generally or within a specific region of the body, a degree of microvascular dysfunction in the patient, a likelihood of microvascular dysfunction, either generally or within a specific region of the body, the expected or actual efficacy of a specific therapeutic intervention for microvascular dysfunction, or a suggested therapeutic intervention for the patient. In one example, the clinical parameter is an expected value for one of left ventricle end-diastolic volume, left ventricle end-systolic volume, left ventricle ejection fraction, microvascular obstruction, and a left-ventricle oedema percentage after a predetermined period of time. Depending on the value of the clinical parameter, an appropriate therapeutic intervention may be selected for the patient. Appropriate therapeutic interventions can include, for example, administration of medications, implantations of medical devices, or assignment of the patient to a medical facility or portion of a medical facility intended for higher risk patients.

FIG. 4 illustrates one example of a method 400 for assessing the results of a therapeutic intervention on the microvascular function of a patient. At 402, a first series of images of a region of interest within the body of the patient are acquired. At 404, an imaging-derived index of microcirculatory resistance is determined from the series of images. At 406, a therapeutic intervention is performed after acquisition of the first series of images. In one example, the region of interest is within a chest of the patient and acquiring the series of images comprises acquiring the series of images before a primary percutaneous coronary intervention.

At 408, a second series of images is acquired of at least a portion of the region of interest after the therapeutic intervention. At 410, a second angiography-derived index of microcirculatory resistance is determined from the second series of images. At 412, a clinical parameter to the patient via a predictive model according to at least the first angiography-derived index of microcirculatory resistance and the second angiography-derived index of microcirculatory resistance. For example, the predictive model can be provided with both indices, or with a single value calculated as a function of the two indices, such as a difference between the two indices or a ratio of the two indices. In this implementation, the clinical parameter will generally represent a likelihood that the patient will experience an adverse event of some form after the therapeutic intervention. In the cardiac example described above, the clinical parameter represents a likelihood that the patient will experience an adverse cardiac condition after the primary percutaneous coronary intervention.

FIG. 5 illustrates an example of a method 500 for assessing microvascular dysfunction of a patient. At 502, a series of images of a region of interest within the body of the patient are acquired with the patient at rest, that is, without providing a vasodilator or after a vasodilator has been provided to the patient. At 504, an imaging-derived index of microcirculatory resistance is determined from the series of images. At 506, a first clinical parameter is assigned to the patient via a first predictive model according to at least the first angiography-derived index of microcirculatory resistance. In the illustrated example, the first clinical parameter is a categorical parameter that can assume a first value representing a presence of microvascular dysfunction, a second value representing an absence of microvascular dysfunction, and a third value representing an indeterminate result.

At 508, it is determined if the result is indeterminate, that is, if the first clinical parameter assumed the third value. If not (N), the method terminates. If so (Y), a vasodilator is given to the patient at 510. A second series of images of the region of interest is acquired at 512, and a second angiography-derived index of microcirculatory resistance is determined from the second series of images at 514. At 516, a second clinical parameter is assigned to the patient via a second predictive model according to at least the second angiography-derived index of microcirculatory resistance. In the illustrated example, the second clinical parameter is a categorical parameter that can assume a first value representing the presence of microvascular dysfunction and a second value representing the absence of microvascular dysfunction.

Figure 6:
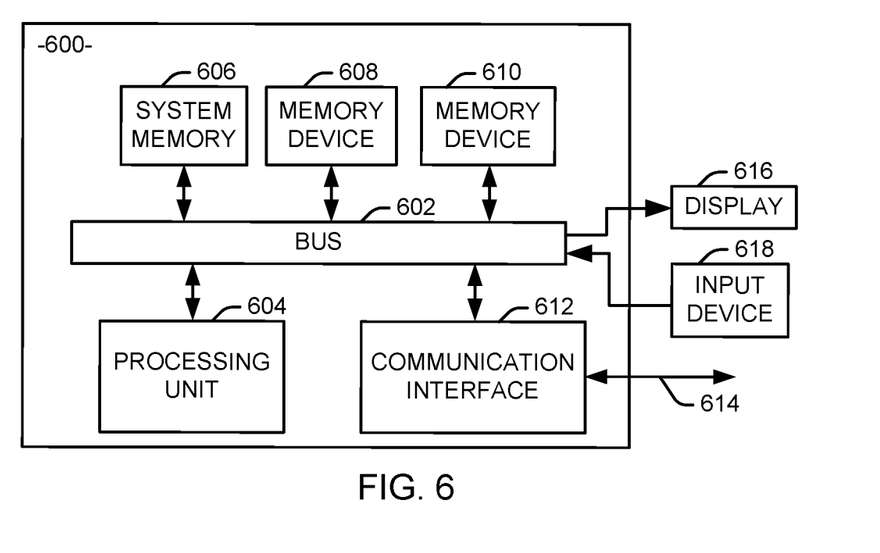
FIG. 6 is a schematic block diagram illustrating an exemplary system of hardware components capable of implementing examples of the systems and methods disclosed herein.

FIG. 6 is a schematic block diagram illustrating an exemplary system 600 of hardware components capable of implementing examples of the systems and methods disclosed herein. The system 600 can include various systems and subsystems. The system 600 can be a personal computer, a laptop computer, a workstation, a computer system, an appliance, an application-specific integrated circuit (ASIC), a server, a server BladeCenter, a server farm, etc.

The system 600 can include a system bus 602, a processing unit 604, a system memory 606, memory devices 608 and 610, a communication interface 612 (e.g., a network interface), a communication link 614, a display 616 (e.g., a video screen), and an input device 618 (e.g., a keyboard, touch screen, and/or a mouse). The system bus 602 can be in communication with the processing unit 604 and the system memory 606. The additional memory devices 608 and 610, such as a hard disk drive, server, standalone database, or other non-volatile memory, can also be in communication with the system bus 602. The system bus 602 interconnects the processing unit 604, the memory devices 606-610, the communication interface 612, the display 616, and the input device 618. In some examples, the system bus 602 also interconnects an additional port (not shown), such as a universal serial bus (USB) port.

The processing unit 604 can be a computing device and can include an application-specific integrated circuit (ASIC). The processing unit 604 executes a set of instructions to implement the operations of examples disclosed herein. The processing unit can include a processing core.

The additional memory devices 606, 608, and 610 can store data, programs, instructions, database queries in text or compiled form, and any other information that may be needed to operate a computer. The memories 606, 608 and 610 can be implemented as computer-readable media (integrated or removable), such as a memory card, disk drive, compact disk (CD), or server accessible over a network. In certain examples, the memories 606, 608 and 610 can comprise text, images, video, and/or audio, portions of which can be available in formats comprehensible to human beings.

Additionally or alternatively, the system 600 can access an external data source or query source through the communication interface 612, which can communicate with the system bus 602 and the communication link 614.

In operation, the system 600 can be used to implement one or more parts of a system in accordance with the present invention, in particular, the feature extractor 114 and the predictive model 116 of FIG. 1 or the microvascular analysis system of FIG. 2. Computer executable logic for implementing the diagnostic system resides on one or more of the system memory 606, and the memory devices 608 and 610 in accordance with certain examples. The processing unit 604 executes one or more computer executable instructions originating from the system memory 606 and the memory devices 608 and 610. The term "computer readable medium" as used herein refers to a medium that participates in providing instructions to the processing unit 604 for execution. This medium may be distributed across multiple discrete assemblies all operatively connected to a common processor or set of related processors.

Specific details are given in the above description to provide a thorough understanding of the embodiments. However, it is understood that the embodiments can be practiced without these specific details. For example, physical components can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps, and means described above can be done in various ways. For example, these techniques, blocks, steps, and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine-readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes but is not limited to portable or fixed storage devices, optical storage devices, wireless channels, and/or various other storage mediums capable of storing that contain or carry instruction(s) and/or data.

In the preceding description, specific details have been set forth in order to provide a thorough understanding of example implementations of the invention described in the disclosure. However, it will be apparent that various implementations may be practiced without these specific details. For example, circuits, systems, networks, processes, and other components may be shown as components in block diagram form in order not to obscure the example implementations in unnecessary detail. In other instances, well-known circuits, processes, algorithms, structures, and techniques may be shown without unnecessary detail in order to avoid obscuring the examples. The description of the example implementations will provide those skilled in the art with an enabling description for implementing an example of the invention, but it should be understood that various changes may be made in the function and arrangement of elements without departing from the spirit and scope of the invention. Accordingly, the present invention is intended to embrace all such alterations, modifications, and variations that fall within the scope of the appended claims.

What is claimed is:

1. A method for assessing coronary microvascular dysfunction of a patient, the method comprising:

acquiring a first series of images of a region of interest within the patient;

determining a first angiography-derived index of microcirculatory resistance from the series of images and a measured first aortic pressure of the patient, wherein determining the imaging-derived index of microcirculatory resistance from the series of images comprises:
measuring the first aortic pressure of the patient;
determining an angiography-derived fractional flow reserve from the series of images;
determining, from the series of images, a transit time of a marker to travel between first and second reference points; and
calculating a product of a ratio of the number of frames necessary for the contrast dye to travel from the guiding catheter to the distal reference to a frame rate of the imager, the first aortic pressure, and the angiography-derived fractional flow reserve determined from the series of images;

assigning a first clinical parameter to the patient via a first predictive model trained on a set of training data representing the first clinical parameter and receiving at least the first angiography-derived index of microcirculatory resistance as an input and providing the first clinical parameter as an output, wherein the first clinical parameter is a categorical parameter that can assume a first value representing a presence of microvascular dysfunction, a second value representing an absence of microvascular dysfunction, and a third value representing an indeterminate result; and performing the following steps if the first clinical parameter assumes the third value:

providing a vasodilator to the patient;

acquiring a second series of images of the region of interest;

determining a second angiography-derived index of microcirculatory resistance from the second series of images and a second measured aortic pressure of the patient; and assigning a second clinical parameter to the patient via a second predictive model trained on a set of training data representing the second clinical parameter and receiving at least the second angiography-derived index of microcirculatory resistance as an input and providing the second clinical parameter as an output, wherein the second clinical parameter is a categorical parameter that can assume a first value representing the presence of microvascular dysfunction and a second value representing the absence of microvascular dysfunction.

* * * * *